United States Patent [19]

Fellmann et al.

[11] Patent Number: 5,026,942
[45] Date of Patent: * Jun. 25, 1991

[54] PROCESS FOR SELECTIVE DIISOPROPYLATION OF NAPHTHYL COMPOUNDS USING SHAPE SELECTIVE ACIDIC CRYSTALLINE MOLECULAR SIEVE CATALYSTS

[75] Inventors: Jere D. Fellmann, Livermore; Robert J. Saxton, Sunnyvale; Paul R. Wentrcek, Redwood City, all of Calif.; Eric G. Derouane, Namur, Belgium; Pascale Massiani, Sunnyvale, Calif.

[73] Assignee: Catalytica, Inc., Mountain View, Calif.

[ * ] Notice: The portion of the term of this patent subsequent to Mar. 26, 2008 has been disclaimed.

[21] Appl. No.: 438,496

[22] PCT Filed: Oct. 5, 1989

[86] PCT No.: PCT/US89/04485
§ 371 Date: Dec. 12, 1989
§ 102(e) Date: Dec. 12, 1989

Related U.S. Application Data

[63] Continuation-in-part of Ser. No. 254,284, Oct. 5, 1988.

[51] Int. Cl.$^5$ .............................. C07C 2/68
[52] U.S. Cl. .......................... 585/467; 585/466
[58] Field of Search ................. 585/466, 467

[56] References Cited

U.S. PATENT DOCUMENTS

| | | | |
|---|---|---|---|
| 3,631,120 | 12/1971 | Eberly, Jr. et al. | 585/467 |
| 4,415,544 | 11/1983 | Kokotailo et al. | 502/60 |
| 4,440,871 | 4/1984 | Lok et al. | 585/467 |
| 4,567,029 | 1/1986 | Wilson et al. | 585/467 |
| 4,891,448 | 1/1990 | Garces et al. | 568/628 |

FOREIGN PATENT DOCUMENTS

| | | |
|---|---|---|
| 294759 | 12/1965 | Australia . |
| 0012514 | 6/1980 | European Pat. Off. . |
| 0202752 | 11/1986 | European Pat. Off. . |

*Primary Examiner*—Patrick P. Garvin
*Assistant Examiner*—E. D. Irzinski
*Attorney, Agent, or Firm*—E. Thomas Wheelock

[57] ABSTRACT

The selective isopropylation of a naphthyl compound to diisopropylnaphthalene enhanced in the 2,6-diisopropylnaphthalene isomer is obtained in the presence of an acidic crystalline molecular sieve catalyst having twelve membered oxygen rings. The catalyst pore aperture dimension range from 5.5 Å to 7.0 Å. The user of these shape selective catalysts results in a diisopropylnephthalene stream which is enhanced in β isomers and enhanced in the desired 2,6-diisopropylnaphthalene isomer. A particularly preferred catalyst is synthetic Mordenite having a specific Si/Al ratio and NMR characteristics. Specific catalyst modifications are also described to improve selectivity to the desired 2,6-diisopropylnaphthalene isomer.

29 Claims, 4 Drawing Sheets

ISOPROPYLATION OF NAPHTHALENE

MONOALKYLATION:

ISOMERIZATION:

DIALKYLATION

TO THE 2,6 ISOMER:

ISOMERIZATION:

α,β ISOMERIZATON

α,α ISOMERIZATON

PROCESS FOR SELECTIVE DIISOPROPYLATION OF NAPHTHYL COMPOUNDS USING SHAPE SELECTIVE ACIDIC CRYSTALLINE MOLECULAR SIEVE CATALYSTS

RELATED APPLICATIONS

This is a continuation-in-part of copending application U.S. Ser. No. 254,284, filed Oct. 5, 1988; the entirety of which is incorporated by notice.

TECHNICAL FIELD

This invention relates generally to isopropylation of naphthyl compounds to obtain diisopropylnaphthalenes, and more specifically this invention relates to the use of shape selective catalysts whose pores are configured to selectively obtain the desired 2,6-diisopropylnaphthalene isomer while minimizing the production of undesirable diisopropylnaphthalene isomers, triisopropylnaphthalenes and tetraisopropylnaphthalenes.

BACKGROUND OF THE INVENTION

A new class of thermoplastic polymers, known as thermotropic liquid crystal polymers ("LCP"), has recently been introduced to the marketplace. These polymers combine the advantageous feature of moldability with multidirectional mechanical strength superior to other thermoplastics formerly available. Generally, these new LCP materials are polyesters made up of planar, linear disubstituted aromatics. Examples of some LCPs currently in use are p-hydroxy-benzoic acid, p-hydroquinone, 4,4'-dihydroxybiphenyl and 2-hydroxy, 6-napthenoic acid.

Other LCPs would appear commercially attractive if either 2,6-dihydroxynaphthalene or 2,6-dicarboxynaphthalene were readily available. Unfortunately, these materials are not commercially produced because cheap, readily available feed stocks do not exist. A viable feed stock, which is convertible into either the dihydroxy or dicarboxy monomers, based upon known technology, is 2,6-diisopropylnaphthalene.

Before proceeding with any description of the isopropylation reaction system, it is important to first review the nomenclature and numbering scheme for the various substituted naphthalene isomers. Equation 1 shows the positional reference numbers. Non-hydrogen bearing carbons are unnumbered because no substitution takes place in these positions.

EQUATION 1

There are two possible isomers which are formed in the monoisopropylation of naphthalene. Substitution occurs only in the 1 and 2 positions and is respectively denoted $\alpha$ and $\beta$. Any monoisopropyl substitution which takes place in positions 3 through 8 identical to the $\alpha$ and $\beta$ positions due to their interrelationship in symmetry.

Multiple naphthalene isopropylation is usually denoted by the position number. Some literature references follow the numbering convention just described, while other references discuss the isomers in terms of the $\alpha$ and $\beta$ terminology. Thus, the 2,6 isomer is the double $\beta$ isomer.

Table 1 describes the statistical distribution of the various diisopropylates using these designations, and assuming that no ortho diisopropylation occurs, e.g., 1,2-, 2,3- and 1,8-diisopropylnaphthalene. In Table 1, it is shown that there are seven disubstituted isomers, of which two of them, (2,6- and 2,7-) are the double $\beta$ product.

TABLE 1

| TYPE | ISOMER | EQUIVALENTS | NORMALIZED FREQUENCY |
|---|---|---|---|
| $\alpha,\beta$ | 1,6 | 1,6 = 4,7 = 2,5 = 3,8 | 2 |
| | 1,7 | 1,7 = 4,6 = 3,5 = 2,8 | 2 |
| | 1,3 | 1,3 = 2,4 = 5,7 = 6,8 | 2 |
| $\alpha,\alpha$ | 1,4 | 1,4 = 5,8 | 1 |
| | 1,5 | 1,5 = 4,8 | 1 |
| $\beta,\beta$ | 2,6 | 2,6 = 3,7 | 1 |
| | 2,7 | 2,7 = 3,6 | 1 |

In any manufacture of diisopropylnaphthalene, it is clear that some monoisopropyl- and triisopropyl-products and a mix of diisopropyl isomers will also be obtained. In any crude diisopropylnaphthalene product which is not particularly enriched in one diisopropylnaphthalene isomer, isomer separation by thermal distillation is very inefficient and difficult because the boiling points of 2,6-diisopropylnaphthalene and 2,7-diisopropylnaphthalene are very close. Similarly, diisopropylnaphthalene isomer separation by fractional crystallization using melting points is inefficient and suffers from yield problems because of the loss of the desired product in the mother liquor, and because of large recycle streams.

The present invention provides a process for reacting a naphthyl compound selected from the group comprising naphthalene, monoisopropylnaphthalene and mixtures thereof, with a propyl containing moiety, preferably propylene, to obtain diisopropylnaphthalene enriched in 2,6-diisopropylnaphthalene, above its expected equilibrium proportion. The shape selective catalyst for this process comprises an acidic crystalline molecular sieve having twelve-membered oxygen rings and pore apertures with dimensions between 5.5Å and 7.0Å. Particularly, preferred shape selective materials are those having specific NMR characteristic which are believed to represent materials having very little non-framework aluminum in the interstices of the materials. Preferably, the 2,6-diisopropylnaphthalene isomer comprises greater than 39 mole percent of the total diisopropylnaphthalenes obtained. It is also preferred that the ratio of 2,6-diisopropylnaphthalene to 2,7-diisopropylnaphthalene in the reaction product is greater than 1.0, preferably greater than 1.2.

Therefore, it is an object of this invention to provide an efficient and selective process for the isopropylation of naphthyl compounds to obtain a higher yield of 2,6 diisopropylnaphthalene in relation to 2,7-diisopropylnaphthalene, while simultaneously minimizing the formation of unwanted byproducts.

It is a further object of this invention to provide shape selective catalysts whose pore size and configuration are designed to maximize the yield of the desired 2,6-diisopropylnaphthalene isomer relative to the sum of the other diisopropylnaphthalenes, while minimizing formation of higher substituted species.

It is still a further object of this invention to provide a process to selectively obtain enhanced levels of 2,6-diisopropylnaphthalene using a naphthyl product feed stream comprising naphthalene, monoisopropylnaphthalene, and mixtures thereof.

These and further objects of the invention will become apparent to those of ordinary skill in the art with reference to the following description.

SUMMARY OF THE INVENTION

A process for obtaining diisopropylnaphthalene enriched in 2,6-diisopropylnaphthalene is described which comprises the steps of providing a naphthyl compound selected from the group comprising naphthalene, monoisopropylnaphthalene and mixtures thereof, and a propyl containing moiety, preferably propylene, to an alkylation reactor. A suitable catalyst is one comprising an acidic crystalline molecular sieve having twelve membered oxygen rings and pore aperture dimensions between 5.5Å and 7.0Å. The naphthyl compound is reacted with a propyl containing moiety such as propylchloride, propylalcohol, or preferably propylene, in the presence of the provided catalyst under conditions sufficient to convert said naphthyl compound and propyl containing moiety to diisopropylnaphthalene. In a preferred embodiment, 2,6-diisopropylnaphthalene comprises at least 39 mole percent of the diisopropylnaphthalenes obtained according to the process. In another preferred embodiment, the ratio of 2,6-diisopropylnaphthalene to 2,7-diisopropylnaphthalene which is obtained according to the process is greater than 1.0, preferably greater than 1.2. Crystalline molecular sieve catalysts are selected from the group comprising MeAPSO-46, Offretite, ZSM-12 and synthetic Mordenite. Preferred catalysts are synthetic Mordenite and ZSM-12, with pore aperture dimensions of 6.5Å, 7.0Å and 5.5Å, 5.7Å and 6.2Å, respectively. These preferred catalysts can be used in the isopropylation reaction without any pretreatment to modify the pore aperture dimensions. Synthetic Mordenite is particularly preferred. An especially desirable material is a synthetic Mordenite which has been dealuminated to a Si/Al ratio between about 5 and 100 (or between 5 and 50) and which display certain characteristic NMR spectra. Also preferred are those materials which have been surface-deactivated in the manner specified below. Other useful catalysts may be obtained by treatment of an acidic crystalline molecular sieve having pore aperture dimensions greater than 7.0Å selected from the group consisting of Zeolite L, Zeolite Beta, faujasite and SAPO-5, to reduce the dimensions of the pore aperture.

DETAILED DESCRIPTION OF THE INVENTION

Before proceeding with a detailed description of the present invention, it is first necessary to define a series of terms which relate to the physical characteristics and configuration of the acidic crystalline molecular sieve catalysts used in the present invention. Much of this terminology arises out of the literature concerning those crystalline aluminosilicate polymers known as zeolites. These acidic crystalline molecular sieve structures are obtained by the building of a three dimensional network of AlO4 and SiO4 tetrahedra linked by the sharing of oxygen atoms. The framework thus obtained contains pores, channels and cages or interconnected voids. As trivalent aluminum ions replace tetravalent silicon ions at lattice positions, the network bears a net negative charge, which must be compensated for by counterions (cations). These cations are mobile and may occupy various exchange sites depending on their radius, charge or degree of hydration, for example. They can also be replaced, to various degrees, by exchange with other cations. Because of the need to maintain electrical neutrality, there is a direct 1:1 relationship between the aluminum content of the framework and the number of positive charges provided by the exchange cations. When the exchange cations are protons, the molecular sieve is acidic. The acidity of the sieve is therefore determined by the amount of proton exchanged for other cations with respect to the amount of aluminum.

Crystalline molecular sieve structures are often defined in terms of the number of their tetrahedral units (T atoms). For example, in sodalite the silica and alumina tetrahedra are linked together to form a cubooctahedron, an octahedron truncated perpendicularly to all C4 - axes. The sodalite unit is built from four and six membered oxygen rings. The mordenite framework is built from chains of tetrahedra cross linked by oxygen bridges. Each Al or Si tetrahedron is, in addition, part of a five-membered oxygen ring. The chains are then interconnected to obtain the mordenite structure. Mordenite is defined as having twelve-membered oxygen rings. The mordenite pore structure consists of elliptical and noninterconnected channels parallel to the c axis of the orthorhombic structure with pore aperture dimensions of 6.5Å and 7.0Å. A more complete characterization of the zeolites can be found in E.G. Derouane, "Diffusion and Shape-Selective Catalysis in Zeolites," *Intercalation Chemistry*, Ed. by Stanley Whittingham (Academic Press, 1982).

ZSM-12 belongs structurally to the Mordenite group of zeolites. The pore structure of ZSM-12 consists of linear, non-interpenetrating channels which are formed by twelve-membered rings and possess pore aperture dimensions of 5.5Å, 5.7Å and 6.2Å. See Jacobs, P.A. et al., "Synthesis of High Silica Aluminosilicate Zeolites," Studies in Surface Science and Catalysis #33, Elsevier, 1987 page 301. See also, Meier, W.M., "Atlas of Zeolite Structure Types" 2nd ed., Structure Commission of the International Zeolite Association, 1987). Offretite is a 12-oxygen ring zeolite with a pore aperture dimension of 6.7Å and 6.8Å in which the structure also contains a 14-hedron cage.

MeAPSO-46 is also a 12-oxygen ring zeolite with a pore aperture dimension of 6.2Å and 6.4Å.

According to the present invention, acidic crystalline molecular sieve catalysts containing twelve membered oxygen rings are useful in the isopropylation reaction of naphthyl compounds.

Pore structure (dimensions and network) varies greatly among zeolites. Without modifications of the zeolite structure, the lowest pore aperture dimension is about 2.6Å and the highest is 7.4Å. Pores may lead to linear, parallel, or interconnected channels or may give access to larger intracrystalline cavities, sometimes referred to as cages. For all zeolites, the pore opening is determined by the free aperture of the oxygen ring that limits the pore aperture.

The free diameter values given in the channel description and on the ring drawings (not shown here) are based upon the atomic coordinates of the type species in the hydrated state and an oxygen radius of 1.35Å, as determined from x-ray crystallographic data. Both minimum and maximum values are given for noncircular apertures. In some instances, the corresponding interatomic distance vectors are only approximately coplanar; in other cases the plane of the ring is not normal to the direction of the channel. Close inspection of the framework and ring drawings should provide qualitative evidence of these factors. Some ring openings are defined by a very complex arrangement of oxygen atoms we have included references to publications which contain extensive drawings and characterization data. The relevant portions of those references are incorporated herein. It should be noted that crystallographic free diameters may depend upon the hydration state of the zeolite particularly for the more flexible frameworks. It should also be borne in mind that effective free diameters can be temperature dependent. Maximum values for the four-, six-, eight-, ten-, and twelve-membered oxygen rings have been calculated to be 2.6Å, 3.6Å, 4.2Å, 6.3Å and 7.4Å, respectively.

As used throughout the instant specification, the term "pore aperture" is intended to refer to both the pore mouth at the external surface of the crystalline structure, and to the intracrystalline channel, exclusive of cages. When a crystalline molecular sieve is hereinafter characterized by a "pore aperture dimension" we intend to adopt the geometric dimensional analysis defined as "crystallographic free diameter of channels" in Meier, W.M., Olson, D.H., Atlas of Zeolite Structure Types, (Butterworth's, 1987, 2d Rev. Ed.) The term "dimension" is preferred over "diameter" because the latter term implies a circular opening, which is not always accurate in crystalline molecular sieves.

Shape selective reactions occur when the zeolite framework and its pore structure allow substrate molecules of a given size and shape to reach active sites located in the intracrystalline free space, and allow product molecules of a given size and shape to diffuse out of the intracrystalline free space. It is therefore important to characterize accurately the pore structure that is encountered in the various crystalline molecular sieve frameworks.

The nature of interconnecting channels in acidic crystalline molecular sieve catalysts is important in determining their physical and chemical properties. Three types of channel systems have been defined: a one dimensional system, such as found in analcime, does not permit intersection of the channels; two dimensional systems can be found in certain zeolites; and, three dimensional systems have intersecting channels. There are two types of three dimensional channels; in one, the channels are equidimensional, i.e., the pore aperture dimension of all the channels is equal, regardless of the direction. The second type consists of three-dimensional, intersecting channels, but the channels are not equidimensional; the pore aperture dimension depends upon the crystallographic direction. See Donald W. Breck, "Zeolite Molecular Sieves: Structure, Chemistry, and Use," at pp. 59-60 (John Wiley & Sons, 1974).

Crystalline molecular sieves With three-dimensional channels can also contain larger intracrystalline cavities known as cages. These cavities may accommodate substrate molecules and, in principal, play a role in shape selective reactions. For example, sodalite has sodalite cages, as does faujasite. Faujasite is a 12-oxygen ring zeolite with a pore aperture dimension of 7.4Å and also has supercages (26hedron) With a cage dimension of 11.8Å. Wide Type A Zeolite has cages having free dimension of 11.4521. See E.G. Derouane, "Diffusion and Shape-Selective Catalysis in Zeolites," Intercalation Chemistry, at pp. 112-114, Ed. by M. Stanley Whittingham (Academic Press, 1982). See also Thaddeus E. Whyte et al., "Catalytic Materials: Relationship between Structure and Reactivity," at pp. 165-167, ACS Symposium Series 248, (American Chemical Society, 1984).

Figure 1:
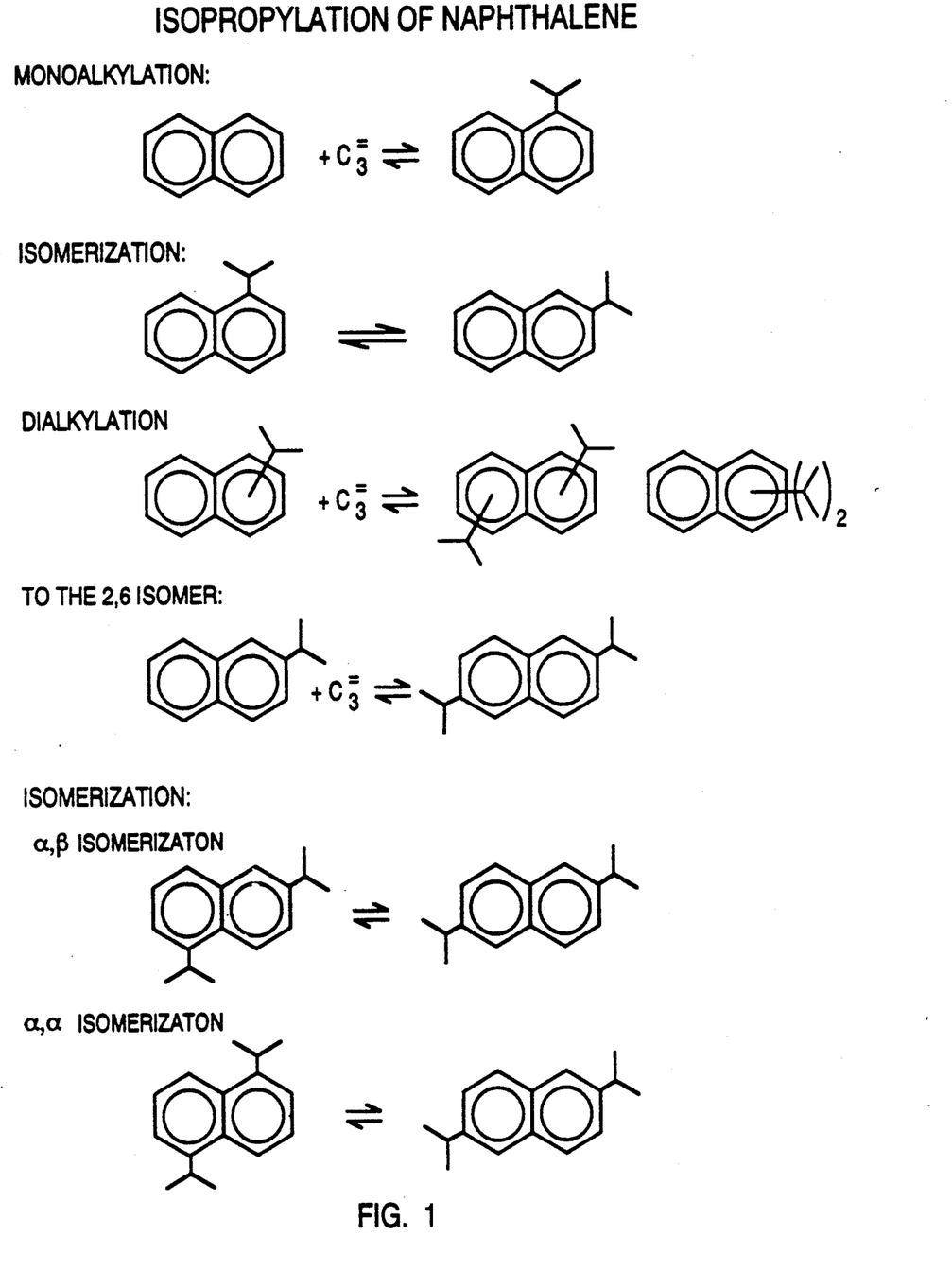
FIG. 1 is a stepwise description of the isopropylation of naphthalene to the mono-, di-, tri and higher polyalkylnaphthalenes.

Having defined some of the terms used to describe the crystalline molecular sieve catalyst component, it is time to turn to the organic substrate for the alkylation reaction system of the instant invention. The substrate is a naphthyl compound selected from the group comprising naphthalene, monoisopropylnaphthalene and mixtures thereof. The isopropylation of naphthalene is known to occur in stepwise manner beginning with monoalkylates, dialkylates, trialkylates, etc. The exact scheme of this progression is set forth more completely in FIG. 1 which also reveals the interconnectivity of the various alkylated species. Of particular interest to the present invention are the different routes and intermediates to the 2,6-diisopropylnaphthalene isomer. This isomer can be formed directly by the $\beta$ isopropylation of the $\beta$-monoalkylate or by isomerization of $\alpha,\alpha$ and $\alpha,\beta$ dialkylates.

The equilibrium data for the monoisopropylation of naphthalene is important since the 2,6 isomer is the $\beta,\beta$ product and because the $\beta$ isomer is the preferred thermodynamic species for the monoalkylate. It has been shown by Olah (U.S. Pat. No. 4,288,646) that the concentration of the $\beta$ product increases with the stearic bulk of the substituent for monoalkylates of naphthalene. See Table 2. This is predicted to hold true for dialkylates as well.

TABLE 2

| Equilibrium Composition of Mono-Alkylnaphthalene | | |
|---|---|---|
| Alkyl | $\alpha$, % | $\beta$, % |
| Methyl | 24.5 | 75.5 |
| Ethyl | 9.5 | 90.5 |
| Isopropyl | 1.5 | 98.5 |
| tert-Butyl | 0 | 100 |

In the prior art, a considerable number of catalysts have been shown to be effective for the monoisopropylation of naphthalene. (See Table 3.) An equilibrium distribution of products for the monoalkylation has been obtained over zeolite catalysts. (Kemme, U.S. Pat. No. 4,026,959.) It is shown that the concentration of the $\beta$ isomer is a function of the nature of the alkylation catalyst and the operating conditions. It has also been shown that the isomerization of $\alpha$ to $\beta$ was dependent upon temperature, catalyst charge, time and substrate water content.

TABLE 3

Monoisopropylation of Naphthalene with Propylene over Various Catalysts

| Catalyst | Solvent | Reaction Temp °C. | α + β Yield | Product Composition % α | β |
|---|---|---|---|---|---|
| Nafion-H | — | 220 | 37 | 10 | 90 |
| HF | heptane | 78 | 91.2 | 3 | 97 |
| H$_3$PO$_4$/ Kieselguhr | — | 200 | 36 | 73 | 27 |
| H$_2$SO$_4$ | — | 10 | 90 | 54 | 36 |
| AlCl$_3$ | — | 100 | — | 4 | 96 |
| RE-Y | — | 218 | 93 | — | — |
| BF$_3$.Et$_2$O | — | −10 | 69 | 70 | 30 |

Few literature references, however, describe catalysts or conditions for the direct preparation of 2,6 diisopropylnaphthalene. Teijin describes the preparation of the di-β product using an AlCl3 catalyst by direct alkylation (Japanese Patent J75011379-B) or via transalkylation (Japanese Patent J75010586-B) Haseltine (U.S. Pat. No. 4,064,068) teaches the equilibrium product composition for about 2:1 propylene/ naphthalene reaction at 120° C. over excess AlCl4. See Table 4.

TABLE 4

Weight and Mole % Products for Diisopropylated Naphthalene

| Alkylate: | Naphthalene | Mono | Di | Tri | Other | Yield Total |
|---|---|---|---|---|---|---|
| Yield, Weight % | 7 | 26 | 53 | 12 | 2 | 88 |
| Yield Mole % | 11 | 30 | 49 | 10 | 1 | — |
| Yield, Mole % Isopropylated Product Composition | — | 33 | 54 | 11 | 1 | — |

For the production of 2,6-diisopropylnaphthalene, there are two important measures of the distribution of diisopropylated species obtained. One is the % of 2,6-diisopropylated naphthalene among all diisopropylated naphthalenes. The other is the ratio of the 2,6- and 2,7-isomers. The values of these measures in an equilibrium distribution of diisopropylated naphthalene species have been determined using silica-alumina, which is a non-shape selective catalyst (see Example 1). A distribution at equilibrium contains 39% 2,6-diisopropylnaphthalene among all diisopropylnaphthalenes and a 2,6-/2,7- isomer ratio of 1.0.

With non-shape selective catalysts, it is believed that the highest % of 2,6-diisopropylnaphthalene among all diisopropylnaphthalenes is at equilibrium, 39%. Therefore, in order to achieve selectivities of the desired 2,6-diisopropylnaphthalene higher than the equilibrium yield, it was recognized that it is first necessary to increase the yield of the β monoisopropylnaphthalene isomer generally, and then to kinetically increase the production of the 2,6 isomer relative to the 2,7 isomer.

According to the present invention, the use of a shape selective acidic crystalline molecular sieve catalyst provides a kinetic distribution of diisopropylnaphthalenes substantially different from the equilibrium distribution. Kinetically, the 2,6 isomer is more rapidly obtained from the β monoisopropylnaphthalene precursor than the 2,7 isomer. Since the β isomer is the precursor for the desired 2,6 isomer, an increase in the amount of β isomer substrate will ultimately improve both the yield and selectivity to the desired 2,6 isomer.

EXAMPLE 1

To determine the percent 2,6-isomer among all diisopropylnaphthalenes and the 2,6-/2,7-isomer ratio in an equilibrium product distribution, naphthalene was alkylated using a non-shape selective catalyst under equilibrium conditions such that thermodynamic equilibration of products was obtained.

90.0 grams naphthalene was alkylated using 10.0 grams SiO$_2$-Al$_2$O$_3$ (Grace) under conditions where the naphthalene/catalyst weight ratio was 9 and the propylene was fed from a heated reservoir at a constant rate of 25 cc/min using a mass flow controller. The temperature of the reaction was 275° C.

TABLE 5

Equilibrium Product Distribution for Naphthalene Alkylation Using SiO$_2$—Al$_2$O$_3$

| Naphth. Conv. | mol % Mono | mol % Di | mol % Poly | 2,6/2,7 Ratio | % 2,6 In Di |
|---|---|---|---|---|---|
| 23.4 | 91.9 | 8.1 | 0.0 | 1.00 | 36.8 |
| 94.2 | 31.1 | 51.5 | 17.4 | 1.03 | 38.5 |

The mole percents mono, di, and polyisopropylnaphthalenes obtained at 94.2% conversion agree excellently with the data of Haseltine, see Table 4. This demonstrates that the 2,6/2,7-isomer ratio and the percent 2,6-isomer among all diisopropylnaphthalenes at this conversion show the same equilibrium distribution (% 2,6 and 2,6/2,7-ratio) among the diisopropylnaphthalenes at lower naphthalene conversion.

The present invention utilizes an acidic crystalline molecular sieve catalyst which has twelve-membered oxygen rings and a pore aperture dimension between 5.5Å and 7.0Å. According to the present invention, a naphthyl compound selected from the group comprising naphthalene, monoisopropylnaphthalene and mixtures thereof, is fed to an alkylation reactor. The naphthyl compound is reacted with a propyl containing moiety, preferably propylene, in the presence of the acidic crystalline molecular sieve catalyst having twelve-membered oxygen rings and a pore aperture width between 5.5Å and 7.0Å, preferably between 6.5Å and 7.0Å. The alkylation reaction is conducted at a propylene/naphthyl compound feed ratio between 0.1 and 10, preferably between 1.0 and 2.0, and elevated temperatures and pressures, generally between 100° C. and 400° C., preferably between 250° C. and 350° C., and between 1 and 100 atmospheres, preferably 1 to 10 atmospheres. These process conditions lead to a diisopropylnaphthalene product which typically contains greater than 39 mole percent diisopropylnaphthalene and a ratio of 2,6-diisopropylnaphthalene to 2,7-diisopropylnaphthalene greater than 1.0. Under optimum catalyst selection and reaction conditions, a ratio of 2,6-diisopropylnaphthalene to 2,7-diisopropylnaphthalene greater than 1.2 can be achieved. In a particularly preferred embodiment, the acidic crystalline molecular sieve catalyst is synthetic Mordenite.

Substantially pure 2,6-diisopropylnaphthalene can be recovered from the diisopropylnaphthalene products in a multi-stage separation scheme. In one embodiment, the diisopropylnaphthalene product is first fractionally distilled to obtain a low boiling fraction which contains unreacted naphthalene and monoisopropylnaphthalene, a middle fraction containing the diisopropylnaphthalenes, and a high boiling fraction containing triisopropylnaphthalene and tetraisopropylnaphthalenes. 2,6-diisopropylnaphthalene is obtained from the middle fraction by cooling the liquid to a temperature between 0° C. and −20° C. to fractionally crystallize the 2,6-isomer from the other diisopropylnaphthalenes. The mother liquor from the crystallization can be subjected to a second crystallization step, or it can then be combined with the low boiling and high boiling fractions, and subjected to transalkylation before recycle to the alkylation reactor, along with fresh naphthalene.

In another embodiment, the recycle stream from the separations section (fractional distillation and crystallization) is combined with a fresh naphthalene feed stream in an equilibration reactor. This recycle mixture containing naphthalene, monoisopropylnaphthalenes, diisopropylnaphthalenes, and higher alkylates is brought to thermodynamic equilibrium over a solid acid catalyst. The equilibrium mixture contains $\beta$ monoisopropylnaphthalene as the predominant product. The equilibrated feed, enriched in B monoisopropylnaphthalene, is then passed to the alkylation reactor where it is combined with propylene at a mole ratio of about one to one.

The use of the term naphthyl compound throughout this specification contemplates both of the above described process schemes, as well as fresh naphthalene feed by itself.

While synthetic Mordenite has been described with reference to a particularly preferred embodiment of the present invention, there are other catalysts which can be used in the alkylation reaction to achieve an alkylation product enriched in both total diisopropylnaphthalenes and in the desired 2,6-diisopropylnaphthalene. When Mordenite is used, only external surface acid site deactivation is required. (See below). ZSM-12 can also be used without modification analogous to Mordenite. Offretite and MeAPSO-46 also fall into the first class of catalysts whose pore aperture dimensions are between 5.5Å and 7.0Å, prior to any modification to the pores.

However, other catalysts may also be considered which have aperture dimensions in excess of 7.0Å. These other catalysts are obtained by a combination of modifications of commercially available, acidic crystalline molecular sieve products. Zeolite L, Zeolite Beta, faujasite and SAPO-5, are twelve membered oxygen rings whose pore aperture dimensions typically exceed 7.0Å. SAPO is an acronym for silicoaluminophosphate molecular sieves, first reported in 1984. U.S. Pat. No. 4,440,871 to B.M. Lok et al. MeAPO is an acronym for metal aluminophosphate molecular sieves reported in U.S. Pat. No. 4,567,029 to S.T. Wilson et al. The numbers following the acronym are arbitrary and bear no relationship to structural numbers used previously in the literature, e.g. ZSM-5. For a more complete characterizations of each of the catalyst members discussed above, please see Flanigen, E.M. et al., *Stud.Surf.Sci.-Cat.*, pp. 103–112. See also E.G. Derouane, "Diffusion and Shape-Selective Catalysis in Zeolites," *Intercalation Chemistry*, at pp. 112–114, Ed. by M. Stanley Whittingham (Academic Press, 1982). *See also.* S.Ernst, *Zeolites*, Vol. 7, p. 458 (1987) for a good discussion of ZSM-12.

The preferred Si/Al ratio in Zeolite L is 3.0. The structure of Zeolite L consists of columns of symmetrical e-D6R-e units crosslinked to others by single oxygen bridges; planar 12membered rings produce wide channels parallel to the c-axis. The pore aperture of zeolite L determined by x-ray crystallography was found to be 7.1Å. A more detailed description of the structure of zeolite L can be found in D.W. Breck, John Wiley & Sons, page 113, 1974.

SAPO-5 is structurally analogous to AlPO$_4$-5. AlPO$_4$-5 is a 12-ring sieve with a pore aperture of 7.3Å. A more detailed description of the structure can be found in J.M. Bennett et al., *Intrazeolite Chemistry*, ACS Symposium Series 218, American Chemical Society, page 79, 109, 1983.

Before discussing any modifications to molecular sieves whose pore aperture dimensions exceed 7.0Å, it is first necessary to discuss the concept of shape selective catalysts generally, and the basis for choosing among the below-described modification procedures.

The use of shape selective catalysts to enhance the conversion of substrate to the desired isomer involves the use of a catalyst whose intracrystalline structure permits diffusion of the substrate and the desired isomer under reaction conditions. According to the present invention, certain catalyst modifications have been found to provide a shape selective catalyst particularly beneficial to the conversion of naphthalene and monoisopropylnaphthalene to the desired 2,6-diisopropylnaphthalene product. Among these modifications are dealumination, calcination, and external and internal surface acid site modifications.

It should be understood that the preferred zeolites may be purchased in cationic form. Typically only an ion exchange is needed to convert these to the hydrogen form. The preferred catalysts, Mordenite and ZSM-12, as well as Offretite and faujasite, can be optimized to yield greater selectivities to the desired 2,6-diisopropylnaphthalene without substantially altering its pore aperture dimensions. One such modification to the preferred catalysts is to dealuminate. Dealumination of acidic crystalline molecular sieve materials can be achieved by exposing the solid catalyst to mineral acids such as HCl. The desired degree of dealumination will dictate the strength of acid used and the time during which the crystalline structure is exposed to the acid. Nevertheless, our desired method of dealumination is via steam treatment followed by a mild acid treatment and calcination (as discussed below).

The preferred steam treatment parameters are as follows:

| Parameter | Range | Preferred | More Preferred |
|---|---|---|---|
| Temperature °C. | 200°–1000° | 300°–700° | 400°–600° |
| total pressure, ATM. | 0.001–15 | 0.001–5 | 0.2–2 |
| carrier gas | flowing gas | inert (N$_2$, He) | None |
| length of time | 0–24 hrs. | 10 min.–4 hr. | 30 min.–1 hr. |
| # of cycles | several | 1–2 | 1–2 |
| steam partial press. ATM. | 0.001–15 | 0.001–5 | 0.1–2 |

After the steam treatment is completed, the next step should desirably be a mild acid treatment or lead.

The preferred acid leach conditions are as follows:

| Parameter | Range | Preferred | More Preferred |
|---|---|---|---|
| Acid type | — | inorganic acid | HCl, HNO$_3$ |
| concentration | — | 0.01–2M | 0.1–1.0 N |
| Temperature °C. | 10–100° C. | 80–100° C. | 100° C. |
| Time | 5 min–24 hrs. | 2–10 hrs. | 2–6 hrs. |

For additional methods of preparing aluminum-deficient zeolites, see J. Scherzer, "The Preparation and Characterization of Aluminum-Deficient Zeolites,"- Thaddeus E. Whyte et al., "Catalytic Materials: Relationship between Structure and Reactivity, " at pp. 156–160, ACS Symposium Series 248, (American Chemical Society, 1984). We have found that although a wide variety of dealuminated zeolitic materials are initially suitable for the isopropylation reaction, only certain materials retain that suitability for prolonged periods. For instance, dealumination techniques employing strong acid leaches typically produce catalysts which initially are very active but are short-lived. In certain circumstances such an activity profile might be desirable, but typically a catalyst with a longer life is preferred.

Zeolites having certain NMR characteristics, in conjunction with the preferred Si/Al ratio discussed below, have been found to be especially suitable for the disclosed process. Specifically, materials in which the ratio of the broad component of the $^{27}$Al—MAS—NMR to the narrow component is less than 5, have been shown to be particularly preferred. (See below CATALYST TESTING AND EVALUATION METHODS.) In general, this ratio can be considered a measure of the non-framework aluminum (from whatever source) found in the interstices of the zeolite as compared to the aluminum in the zeolite framework.

One method of dealumination which has been found to produce such a preferred material is a steam treatment (in one or more stages) followed by a mild acid leach.

Dealumination according to the instant invention is intended to achieve Si/Al ratio between 5 and 100, preferably between 5 and 50, most preferably, at leat 15 to 35. Additionally, the noted $^{27}$Al—MAS—NMR ratio for these materials is desirably between 0 and 5, preferably between 0 and 2, and most preferably between 0 and 1. Dealumination can also be applied to the second class of molecular sieve materials whose pore aperture dimensions exceed 7.0Å.

A dealuminated crystalline molecular sieve can be calcined at temperatures between 400° C. and 1000° C. preferably between 400° C. and 600° C. Calcination serves to dehydrate or "heal" Si—OH bonds or "nests'- 'after dealumination. Healing these nests provides for a more uniform pore structure within the crystalline material, leading to structural stability and ultimately resulting in improved selectivity.

The calcination conditions of a catalyst can critically effect the catalytic activity. The selection calcination gas, for example oxygen or nitrogen, can effect catalyst species differently. In general, calcination temperatures for crystalline molecular sieve catalysts can vary from 300° C. to 1000° C. For a Zeolite like Hydrogen Mordenite, the optimal temperature ranges was found experimentally to lie between 400° C. and 600° C., but preferentially at 500° C. (Mathur, Kuldeep, Narain, Ph.D. Thesis, University of Pittsburgh, 1977). In the case of H-Mordenite, removal of extra and intra crystalline water can be accomplished effectively in presence of an atmosphere of oxygen or nitrogen. This, however, would not be true in the case of organic residues present on the catalyst, as in a surface treated catalyst. In this case, the calcination temperature and the calcination gas are both important. In the presence of organic residues, preferably, a nitrogen atmosphere is first used so that a minimal amount of water is obtained when bringing the catalyst to calcination temperature. After a sufficient time to carbonize the organic residue, the atmosphere is changed to oxygen at a temperature sufficient to combust the carbonized residue to $CO_2$ while minimizing water formation.

Another catalyst treatment (without regard to the pore aperture dimension of the starting material, thereby inclusive of both the classes of catalysts discussed herein), according to the present invention, involves catalyst external surface acid site removal or blockage. The reason for external surface acid removal or blockage is that inactivating the external surface of Zeolite catalyst will increase its shape-selective character as otherwise, the external surface acts as a non-shape selective catalyst. An additional reason for external surface acid site blockage or removal relates to caking on the catalyst surface. While benzene produces only a small amount of coke on the catalyst surface because of the high stability of the aromatic ring, unsaturated intermediates, such as cyclohexane, cyclohexene and cyclohexadiene are able to condense on the acidic function of the catalyst surface producing a substantial amount of coke. See, Studies in Surface Science and Catalysis, 34, p. 143. Coke will also be formed at the catalyst pores mouth over time. This buildup will cause the pores to become less accessible to substrate molecules, and eventually close the pores, rendering these channels inactive.

When using catalysts obtained by the treatment of crystalline molecular sieve, whose pore aperture dimensions are initially above 7.0Å, internal acid site modification is used to reduce the pore aperture dimension to an extent which shows an enhanced 2,6-diisopropylnaphthalene concentration above its equilibrium value. Unfortunately, we have not presently obtained physical characterization data for the pore aperture dimensions of the modified species. Instead, catalysts with reduced pore aperture dimensions are best described with reference to their performance in the isopropylation reaction under consideration. Those crystalline molecular sieves which have been adequately modified by internal acid site treatment will perform in the selective isopropylation of naphthalene to provide a diisopropylnaphthalene which contains at least 39 mole percent of 2,6-diisopropylnaphthalene, and a 2,6-/2,7-diisopropylnaphthalene mole ratio greater than 1.0.

Generally speaking, crystalline molecular sieves may be treated to modify internal acid sites by contact with a deactivating reagents selected from the group consisting of the halogen, hidrotic and organic derivatives of Groups IIIA, IVA, IVB and VA. Preferred embodiments of the internal acid site deactivating reagents include $B_2H_6$, $SiH_4$ and $PH_3$. For a more complete discussion of the internal acid site modification techniques, see A. Thijs et al., *J. Chem. Soc. Faraday Trans.*, 79, 2821 (1983). See also, J. philippaerts et al., "The Implantation of Boron-Nitrogen Compounds in Mordenite LP and Their Influence on the Adsorption Properties," *Stud. Surf. Sci. Catal.*, 28, 1986, pp. 305–310. The relevant portions of both references being hereby incorporated into this specification.

In addition to the use of the above described deactivating reagents, which tend to be non-specific, there is an intermediate level of crystalline molecular sieve modification which can be used to perform "pore mouth engineering." These reagents provide an intermediate level since they are not specific for external acid site, but are not entirely non-specific, leading to substantial internal acid site modification. In selecting an intermediate deactivating reagent, the characteristics and pore aperture dimensions of the starting crystalline molecular sieve must be matched against the molecular dimensions of the deactivating reagent.

It has been shown that chemical vapor deposition of $Si(OCH_3)_4$ on H-mordenite can be successfully used to control the intracrystalline pore aperture without substantially affecting the catalyst's internal surface acidic properties. $Si(OCH_3)_4$ can be deposited irreversibly on zeolite, without entering the intracrystalline pores. See Niwa, M. et al., *J. Chem.Soc., Faraday Trans.*, 1, 1984, 80, 3135-3145; Niwa, M. et al., "Modification of H-Mordenite by Vapour-phase Deposition Method," J. Chem.Soc.Commun.. 1982, pp. 819-20.

Similarly, chemical vapor deposition of deactivating metal chlorides such as $SiCl_4$, $GeCl_4$, $TiCl_4$ and $SnCl_4$ can be effective to modify pore mouth structures without inactivating internal surface acid sites. These metal molecules, with a range of molecular dimensions, can be selected to be larger than the catalyst pore aperture, thereby preventing substantial diffusion into the internal pore. See Hidalgo, C.V. et al., *Zeolites*, 1984, 4, April, p. 175-180.

It is also recognized that the deactivating agents can be contacted with the molecular sieve in either solution or vapor phase.

As noted above, it is desireable in any case to deactivate external surface acid sites, without regard to the pore aperture dimensions of the starting crystalline molecular sieve, to prevent non-shape selective reactions on the external surface. External surface acid site deactivation can be obtained by either acid site blockage or acid removal. One major limitation of both techniques, however, is that the deactivating agent should be selected to preclude internal surface diffusion. This limitation is easily met by the use of deactivation agents in either liquid or gas phase, whose molecules are too large to fit within even the largest pores of known zeolites. One such molecule is triphenylchlorosilane. See Martens, J.A. et al., *Zeolites*, 1984, 4, April, p. 98-100.

In another embodiment of external surface acid site modifications, it is sometimes necessary to fill the intracrystalline pores with a hydrocarbon to obtain an internally protected catalyst. Thereafter, either an aqueous acid or complexing agent, which is insoluble in the hydrocarbon contained within the intracrystalline pore, is contacted with the protected catalyst. Once the external surface has been deactivated, then the hydrocarbon is removed intracrystalline pores. In EP 86543, a nonpolar organic substance is added to the zeolite to fill its pores. Subsequently, a deactivating agent solution (in polar solvent) is introduced to the catalyst. Alkali metal salt solutions, acting as ion exchange atoms to remove the acidic proton associated with aluminum, are described as suitable deactivating agents. See also U.S. Pat. No. 4,415,544 which teaches the use of paraffin wax to seal off the pores prior to surface treatment with hydrogen fluoride, which remove the aluminum.

Having described a broad range of catalyst modifications, it is necessary to indicate that a combination of some or all of these techniques can be considered in providing an optimized isopropylation catalyst. In the claims appended hereto, we have attempted to indicate a preferred chronological order of treatment steps based upon the starting material, but is not our intent to be limited to a particular order or combination of modifications.

CATALYST TESTING AND EVALUATION METHODS

A stirred, 300 cc Autoclave Engineers autoclave was chosen for this work. It is conveniently operated and was suitable for the purposes of screening for selectivity improvements.

In the autoclave reactor the propylene feed system consisted of a heated reservoir of propylene gas. The propylene was manually introduced into the reactor so that a constant pressure was maintained. In this way the propylene was fed as fast as the catalyst could consume it.

A typical run involved 90 grams of naphthalene and 1.0 g zeolite catalyst or 123 grams $\beta$-isopropylnaphthalene and 1.0 g zeolite. In a standard alkylation reaction the autoclave was charged with either feed and the catalyst. The contents were flushed with nitrogen several times then pressured to 12 psig with nitrogen. With slow stirring the autoclave was heated to the desired reaction temperature at which time stirring was increased to the maximum setting (ca. 3200 rpm). Propylene was then added from a heated reservoir to a constant pressure of ca. 70 psig. Samples were taken every hour and analyzed by GC.

The reaction temperature range was preferably between 200-300° C. However, as low as 100° C. and as high as 400° C. could be considered.

H-Mordenite catalysts were characterized by $^{29}Si$ MAS and CPMAS and $^{27}Al$ MAS NMR using a Bruker MSL-400 spectrometer.

The distribution of framework and non-framework aluminum in the mordenite samples was determined by $^{27}Al$ MAS NMR. All spectra were obtained on a Bruker MSL400 spectrometer. The resonance frequency for aluminum was 104.261 MHz. Samples were spun at 10 kHz in 4mm zirconia rotors in a Bruker double air bearing CPMAS probe. The radio frequency power was adjusted to give a 7 $\mu$sec 90° pulse on an aqueous solution of $AlCl_3$. The signal from this solution sample was also used as a chemical shift reference and set to 0.0 ppm. An excitation pulse length of 3 2 $\mu$sec (35 tip angle) was used for all experimental determinations of aluminum distribution. Shorter (1-2 $\mu$sec) and longer (>5 $\mu$sec) excitation pulses were tested and found to give unreliable aluminum distributions. A spectral width of 100 kHz was used. 1000 free induction decays (FID's) were coadded to produce the final spectrum. Spectrometers used for such measurements must meet certain criteria. The primary requirement is a fast recovery receiver/probe combination (ringdown of 5 $\mu$sec or less) to allow the observation of broad linewidth components in the aluminum spectrum.

The exact procedure for determining aluminum distribution is as follows. The $^{27}Al$ MAS NMR spectrum of the sample is obtained per the description above. The FID may contain two components; a fast decaying signal (linewidth typically 20 kHz) and a slow decaying component (linewidth typically 1 kHz). Fourier transformation of the FID's show that the narrower signal has a chemical shift of 54-55 ppm whereas the broad signal has a chemical shift of approximately 0 ppm. The narrower component corresponds to the aluminum in the zeolite framework. The broader signal corresponds to the non-framework aluminum. Quantitation of the relative amounts of each component is accomplished by graphical evaluation of the FID's. "Perspectives in Molecular Sieve Science", ed. W.H. Flank and T.E.

Whyte, ACS Series 368, 1988, pp. 2032. The narrow and broad components are extrapolated back to zero time and the initial intensity of each component is then determined. The ratio of the intensities of the broad component to the narrower component, B/N, is then calculated. Thus, a zeolite with little non-framework aluminum present will have a small value for B/N. A sample with a large B/N will have significant amounts of the aluminum in the sample present as non-framework species.

Throughout the specification we will use the shorthand notation "NMR ratio" to mean this B/N value.

Si/Al ratios were obtained using ICP analyses. Surface area data were obtained using BET nitrogen adsorption measurements.

Solid state MAS and CPMAS NMR can be particularly useful in determining the effectiveness of calcination. Calcination serves to dehydrate or "heal" Si-OH bonds or "nests". Healing these nests provides for a more uniform pore structure, which improves selectivity, and also gives a more stable structure. From the CPMAS spectra we observed only those silicon atoms which were in close proximity to protons. Typically, this requires that the silicon be either a siloxyl silicon or within a few angstroms of a siloxyl group. Thus, the intensity of the silicon resonance is a direct measurement of the amount of Si—OH bonds present in the zeolite. As the calcination temperature is increased, the intensity of the peak decreases. The CPMAS spectrum of a dealuminated mordenite calcined at 400° C. exhibits a noticeable silicon resonance indicating a significant amount of Si—OH nests remaining in the structure. The CPMAS spectrum of a similar mordenite calcined at 500° C. contains only a negligible peak which indicates a near absence of Si—OH nests.

EXAMPLE 2

Ten grams of Toyo Soda H-Mordenite was loaded in a fritted quartz tube and placed vertically in a tube furnace. A slow helium flow of about 200 cc/min was introduced and the furnace heated to 400° C. At 400° C. steam-saturated helium was introduced at a flow rate of about 1.5 liters/minute. After thirty minutes the steam was discontinued, the helium flow was lowered to about 200 cc/min and the furnace cooled to room temperature. The solid was then transferred to a 500 mL round-bottom flask equipped with a condenser and a stir bar. Two-hundred milliliters of 0.5 N hydrochloric acid was introduced and the resultant mixture refluxed for four hours. After cooling, the solution was filtered and washed with distilled water until the filtrate was free of chloride ions by a $AgNO_3$ test. The solid was first dried at 110° C. for two hours then calcined at 500° C. for eight hours.

If desired, the solid can be subjected to a number of steam calcination and acid washing cycles. After drying the solid at 110° C. the solid can be reintroduced to the fritted quartz tube for an additional steam calcination.

TABLE 6

Comparison of Catalyst Performance and Properties As a Function of Steam Dealuminated/Acid Wash Cycles and Final Calcination Temperature
Naphthalene Isopropylation Reactions

| Catalyst Type[1] | Si/Al Ratio | Conv % | mol % Mono | mol % Di | mol % Poly | 2,6/2,7 Ratio | % 2,6 in Di |
|---|---|---|---|---|---|---|---|
| One Cycle, 400° C. | 24.6 | 35.6 | 81.0 | 18.9 | 0.70 | 2.91 | 67.9 |
|  |  | 94.7 | 30.7 | 66.2 | 2.98 | 2.29 | 59.6 |
| Two Cycles, 400° C. | 35.2 | 15.4 | 90.4 | 9.5 | 0.0 | 2.90 | 67.1 |
|  |  | 37.2 | 81.1 | 18.9 | 0.0 | 2.33 | 63.1 |
| One Cycle, 500° C. | 20.8 | 43.4 | 74.6 | 25.3 | 0.0 | 2.72 | 64.1 |
|  |  | 92.6 | 34.9 | 60.3 | 4.71 | 2.35 | 57.8 |

[1]Catalyst type denotes the preparation of the catalyst. The number of cycles refers to steam calcination/acid washing cycles on Toyo Soda H-Mordenite as explained above. The temperature refers to the final calcination temperature. Each calcination was done for eight hours.

These results show that synthetic Mordenite which has been dealuminated by steam, acid washed, and calcined provides a distribution of diisopropylnaphthalenes having a percent 2,6-isomer (ca. $\geq 60\%$) and a 2,6/2,7 isomer ratio $\geq 2.3$), far superior to an equilibrium distribution (39% and 1.0, respectively). These results also show very low production of poly isopropylnaphthalenes even at very high conversions, example <5% poly- at >90% conversion; compare 17.4% poly at 94.2% conversion using silica-alumina in Example 1.

EXAMPLE 3

Toyo Soda or Norton H-Mordenite were dealuminated following a procedure similar to that of Niwa (*Chem Lett.* 1987, 1637). Five grams of zeolite were dealuminated with a hydrochloric acid solution at 93° C. After dealumination, the solution was filtered and the solid washed with distilled water until no chloride was detected with a $AgNO_3$ solution, followed by drying at 120° C. and calcining at 500° C. for one hour.

TABLE 7

Comparison of Catalyst Performance and Properties As a Function of Acid Wash Treatments For the Naphthalene Isopropylation Reaction

| Mordenite Manufacturer | Si/Al Ratio | Conv | mol % Mono | mol % Di | mol % Poly | 2,6/2,7 Ratio | % 2,6 in Di |
|---|---|---|---|---|---|---|---|
| Norton, (8M HCl)[1] | 28.2 | 8.7 | 89.5 | 10.5 | — | 4.22 | 80.9 |
| Toyo Soda, (0.5M HCl) | 21.4 | 16.1 | 91.2 | 8.8 | — | 2.93 | 68.5 |
|  |  | 54.5 | 73.9 | 25.7 | 0.46 | 2.51 | 60.4 |

[1]Concentration of HCl used for acid dealumination

These results show that synthetic Mordenites from various sources which have been dealuminated by acid wash and calcined give a diisopropyl naphthalene product distribution enriched in the 2,6 isomer ($\geq 60\%$) and having a high 2,6/2,7 isomer ratio ($\geq 2.5$).

propylnaphthalenes with inferior 2,6-isomer content and higher production of poly isopropylnaphthalenes.

EXAMPLE 4

TABLE 8

Comparison of Catalyst Performance As a Function of Si/Al Ratio
Naphthalene Isopropylation Reactions

| H-Mordenite[a] Manufacturer | Si/Al Ratio | Conv. % | mol % Mono | mol % Di | mol % Poly | 2,6/2,7 Ratio | % 2,6 in Di |
|---|---|---|---|---|---|---|---|
| Toyo Soda[1] | 20.8 | 43.4 | 74.6 | 25.3 | 0.0 | 2.72 | 64.1 |
|  |  | 92.6 | 34.9 | 60.3 | 4.71 | 2.35 | 57.8 |
| Toyo Soda[2] | 24.6 | 35.6 | 81.0 | 18.9 | 0.70 | 2.91 | 67.9 |
|  |  | 94.7 | 30.7 | 66.2 | 2.98 | 2.29 | 59.6 |
| Toyo Soda[3] | 35.2 | 15.4 | 90.4 | 9.5 | 0.0 | 2.90 | 67.1 |
|  |  | 37.2 | 81.1 | 18.9 | 0.0 | 2.33 | 63.1 |
| Toyo Soda[4] | 21.4 | 16.1 | 91.2 | 8.8 | 0.0 | 2.93 | 68.5 |
|  |  | 54.4 | 73.9 | 25.7 | 0.46 | 2.51 | 60.4 |
| Toyo Soda[5] | 8.7 | 3.1 | 100.0 | 0.0 | 0.0 | — | — |
|  |  | 46.4 | 82.3 | 17.5 | 0.26 | 2.10 | 47.4 |
| Norton[6] | 28.2 | 5.7 | 100.0 | — | — | — | — |
|  |  | 8.7 | 89.5 | 10.5 | — | 4.22 | 80.9 |
| LGP[7] (as received) | 38.4 | 34.5 | 81.0 | 18.5 | 0.16 | 2.85 | 65.8 |
|  |  | 73.3 | 58.0 | 39.3 | 2.07 | 2.65 | 64.2 |

[a]Types of Treatments:
[1]One cycle steam calcining/0.5 M HCl wash dealumination; 500° C. calcining for eight hours.
[2]One cycle steam calcining/0.5 M HCl wash dealumination; 400° C. calcining for one hour.
[3]Two cycles steam calcining/0.5 M HCl wash dealumination; 400° C. calcining for one hour.
[4]One 0.5 M HCl wash only; 400° C. calcining for two hours.
[5]H-Mordenite without dealumination
[6]Zeolon-100 H-mordenite treated with 8 M HCl at 96° C. for 24 hours followed by calcining at 500° C. for one hour.
[7]Zeocat Z-4060 as received.

These results show that the performance of Mordenite catalyst in the process of this invention may be further improved by dealumination and calcination.

EXAMPLE 5

TABLE 9

Comparison of Naphthalene and Monoisopropylnaphthalene Isopropylation Reactions Using Dealuminated Mordenite and Silica-Alumina Catalysts

| Catalyst | Feed | Temp | Conv | mol % Mono | mol % Di | mol % Poly | 2,6/2,7 Ratio | % 2,6 in Di |
|---|---|---|---|---|---|---|---|---|
| Toyo Soda[1] H-Mordenite | Naphthalene | 275 | 95.1 | 29.1 | 60.3 | 4.71 | 2.50 | 60.8 |
|  |  |  | 76.3 | 55 | 42.9 | 1.74 | 2.65 | 63.2 |
| Toyo Soda[1] H-Mordenite | Monoisopropyl Naphthalene[2] | 275 | 86.0 | 18.0 | 76.1 | 3.15 | 2.55 | 65.0 |
|  |  | 290 | 90.4 | 13.9 | 79.1 | 4.53 | 2.36 | 62.0 |
| SiO$_2$/Al$_2$O$_3$[2] | Naphthalene | 275 | 73.0 | 61.5 | 31.4 | 7.1 | 1.2 | 23.0 |

Footnotes:
[1]Toyo Soda H-Mordenite dealuminated with one cycle steam calcining/0.5 N HCl acid wash; calcined at 500° C. for 8 hr.
[2]The β/ monoisopropylnaphthalene ratio in the feed was greater than 10:1.

These results show that diisopropylnaphthalene products similarly enriched in 2,6-diisopropylnaphthalene are obtained from either naphthalene or β-isopropylnaphthalene as reaction substrate, using the shape selective catalysts of the instant invention. The results further show that the non-shape selective silica-alumina catalyst under the same conditions provides diisopropylnaphthalenes with inferior 2,6-isomer content and higher production of poly isopropylnaphthalenes.

EXAMPLE 6

90.0 grams naphthalene was alkylated using 2.0 grams H-ZSM-5 under a constant propylene feed rate of 75 cc/min from a heated reservoir using a mass flow controller. The temperature of the reaction was 275° C. Two different identical reactions were run substituting H-Zeolite L or H-Zeolite Beta.

In separate experiments, 90.0 grams naphthalene was alkylated under a constant propylene pressure of ca. 70 psig at 275° C. using 1.0 gram of either Toyo Soda H-mordenite dealuminated by refluxing with 0.5 M hydrochloric acid for four hours or H-ZSM-12 and both calcined at 400° C. for eight hours.

TABLE 10

Comparison of Naphthalene Alkylation Reactions Using Dealuminated H-Mordenite, H-ZSM-5, H-Zeolite L or H-Zeolite Beta

| Catalyst | Oxygen Ring | Pore Aperture | Conv. | mol % Mono | mol % Di | mol % Poly | 2,6/2,7 Ratio | % 2,6 in Di |
|---|---|---|---|---|---|---|---|---|
| H-Mordenite | 12 | 6.5,7.0 | 16.1 | 91.2 | 8.8 | 0.0 | 2.93 | 68.5 |
|  |  |  | 54.5 | 73.9 | 25.7 | 0.46 | 2.51 | 60.4 |
| H-ZSM-12 | 12 | 5.5,5.7, 6.2 | 17 | 95 | 5 | 0 | 1.67 | 40 |
| H-Zeolite L | 12 | 7.1 | 69.0 | 77.8 | 20.6 | 1.6 | 0.82 | 21.8 |
| H-Zeolite Beta[1] | 12 | 6.0,7.3 6.8,7.3 | 63.0 | 71.8 | 26.1 | 2.1 | 1.03 | 36.6 |

TABLE 10-continued

Comparison of Naphthalene Alkylation Reactions Using Dealuminated H-Mordenite, H-ZSM-5, H-Zeolite L or H-Zeolite Beta

| Catalyst | Oxygen Ring | Pore Aperture | Conv. | mol % Mono | mol % Di | mol % Poly | 2,6/2,7 Ratio | % 2,6 in Di |
|---|---|---|---|---|---|---|---|---|
| H-ZSM-5 | 10 | 5.3,5.6 5.1,5.5 | 10.0 | 84.0 | 12.0 | 4.0 | 0.14 | 8.3 |

[1]Newsam, J. M. et al., "Structural Characterization of Zeolite Beta" submitted to the Proceedings of the Royal Society, March 31, 1988. Zeolite Beta exist as two polymorphs whereby Polymorph A has a pore aperture of 6.0Å and 7.3Å, and Polymorph B has a pore aperture of 6.8Å and 7.3Å.

The data in Table 10 illustrate the superiority of 12 ring zeolites having pore apertures of 5.5Å to 7.0Å (for example, Mordenite and ZSM-12) over a 10-ring zeolite (ZSM-5) and over 12-ring zeolites having larger pore apertures (for example, Zeolite L and Zeolite Beta) in the isopropylation of naphthalene to produce diisopropylnaphthalene enriched in 2,6-isomer. Only the 12-ring zeolites having pore apertures of 5.5Å to 7.0Å gave both >39% 2,6-diisopropylnaphthalene among all diisopropylnaphthalene and 2,6/2,7 isomer ratio >1.0.

To further demonstrate the desirable nature of certain of the catalysts within the scope of the present invention, a series of catalysts based on synthetic Mordenite were produced having different Si/Al ratios; the higher ratios being produced by the process specified in EPA 0,317,907, published May 31, 1989. One set of catalysts is within the desired Si/Al ratio of the invention desired in EPA 0,317,907 and the other set is outside.

EXAMPLE 7

Three samples of synthetic H-Mordenite were dealuminated using a procedure similar to that shown in Example 2, i.e., the zeolites were steamed, leached in 0.5 N hydrochloric acid for four hours, and calcined in air. The particulars of the specific dealumination steps are as follows:

| Example No.* | Steam** @ T° | Calcination |
|---|---|---|
| 7(a) | Steam in He @ 400° C. | 500° C. for 12 h in air |
| 7(b) | Steam in He @ 400° C. | 500° C. for 16 h in air |
| 7(c) | Steam in He @ 600° C. | 500° C. for 8 h in air |

*The acid treatment step took place between steaming and calcination steps.
**Each steaming step was 30 minutes long.

Each of the dealuminated samples was then measured for Si/Al ratio using the methods discussed above. The values are as follows:

TABLE 11

| Example No. | Si/Al Ratio |
|---|---|
| 7(a) | 19 |
| 7(b) | 25 |
| 7(c) | 30 |

EXAMPLE 8

Each of the samples in Example 7 were then tested for activity in a manner similar to that discussed above. Into a stirred 300 cc. autoclave were introduced 90 grams of naphthalene and 1.0 gram of zeolite sample. After an initial pressurization of nitrogen, the autoclave was heated to 275° C. Propylene gas was continuously introduced and the reactor pressure was manually maintained at about 110 psig. The reactor temperature was maintained at about 275° C. Samples were taken about once an hour and analyzed using a gas chromatograph.

The results from the runs using each of the three catalysts are shown below.

TABLE 12

Results of isopropylation of naphthalene using the Example 7(a) mordenite catalyst (Si/Al = 19)

| Reaction Time (Hrs) | Conversion | % Mono | % di | % other | 2,6/2,7 ratio | 2,6/DiPN % |
|---|---|---|---|---|---|---|
| 0 | — | — | — | — | — | — |
| 0.5 | 44.5 | 76.1 | 23.8 | .1 | 3.07 | 69.0 |
| 1.5 | 71.0 | 60.2 | 39.8 | 0 | 2.56 | 63.0 |
| 2.0 | 78.0 | 52.0 | 46.8 | 1.1 | 2.53 | 61.3 |
| 3.0 | 86.3 | 43.7 | 54.8 | 1.3 | 2.36 | 59.0 |
| 4.0 | 91.6 | 35.8 | 61.7 | 2.3 | 2.28 | 57.5 |
| 5.0 | 94.6 | 29.5 | 67.1 | 3.1 | 2.28 | 56.7 |
| 6.0 | 95.0 | 28.6 | 67.1 | 3.5 | 2.07 | 54.4 |
| 7.0 | 96.1 | 25.8 | 70.0 | 3.9 | 2.00 | 53.4 |

TABLE 13

Results of isopropylation of naphthalene using the Example 7(b) mordenite catalyst (Si/Al = 25)

| Reaction Time (Hrs) | Conversion | % Mono | % di | % other | 2,6/2,7 ratio | 2,6/DiPN % |
|---|---|---|---|---|---|---|
| 0 | — | — | — | — | — | — |
| 0.5 | 27.1 | 83.1 | 16.4 | 0.0 | 3.02 | 69.8 |
| 1.5 | 46.9 | 73.1 | 27.0 | 0.0 | 2.84 | 66.2 |
| 2.5 | 55.0 | 65.7 | 33.8 | 0.5 | 2.44 | 62.6 |
| 3.5 | 77.6 | 52.4 | 46.5 | 1.1 | 2.57 | 61.5 |
| 4.5 | 85.0 | 44.7 | 53.7 | 1.6 | 2.52 | 60.1 |
| 6.5 | 92.2 | 32.4 | 64.6 | 2.6 | 2.39 | 52.9 |

TABLE 14

Results of isopropylation of naphthalene using the Example 7(c) mordenite catalyst (Si/Al = 30)

| Reaction Time (Hrs) | Conversion | % Mono | % di | % other | 2,6/2,7 ratio | 2,6/DiPN % |
|---|---|---|---|---|---|---|
| 0 | — | — | — | — | — | — |
| 0.5 | 28.8 | 78.7 | 21.3 | 0 | 2.99 | 69.8 |
| 1.5 | 48.2 | 66.5 | 33.0 | 0.5 | 2.72 | 66.0 |
| 2.5 | 66.7 | 57.0 | 42.2 | 0.7 | 2.56 | 62.9 |
| 3.5 | 78.4 | 49.0 | 49.8 | 1.1 | 2.46 | 61.3 |
| 4.5 | 82.0 | 44.4 | 53.7 | 1.7 | 2.55 | 61.3 |
| 5.5 | 85.0 | 41.1 | 56.7 | 2.0 | 2.48 | 60.0 |
| 6.5 | 87.5 | 39.4 | 58.3 | 2.2 | 2.65 | 58.6 |

Figure 2:
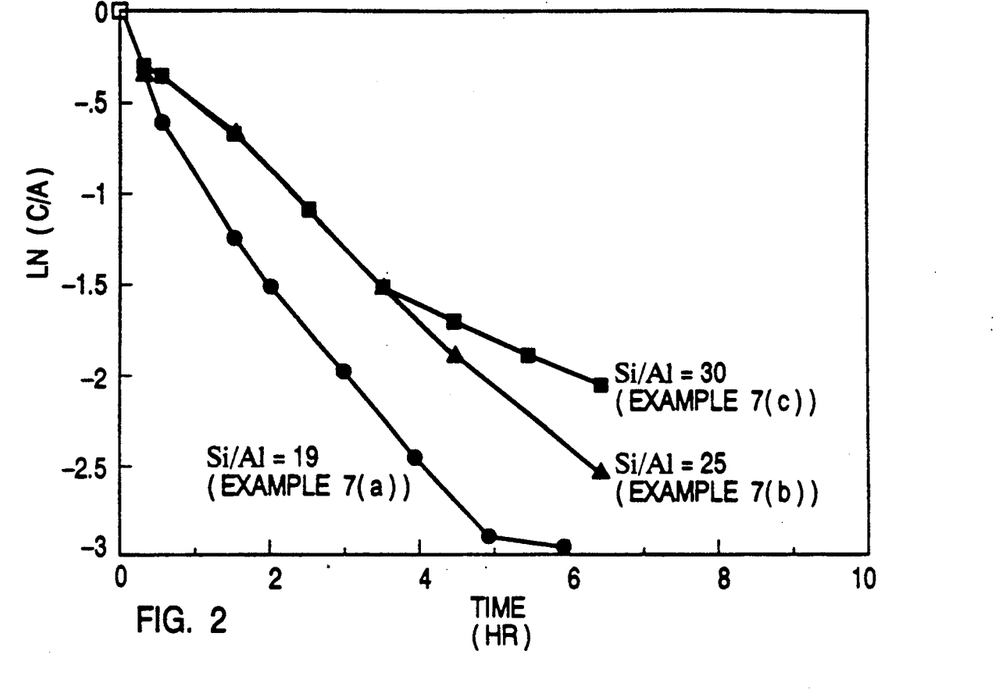
FIGS. 2–6 are plots of the log of naphthalene conversion versus time for a number of different catalysts where naphthalene conversion is expressed as the natural logarithm of the naphthalene molar concentration remaining divided by the initial naphthalene molar concentration.

The conversions for each of these catalysts are displayed in FIG. 2 as the natural logarithm of the naphthalene conversion, i.e., the ratio of the concentration of naphthalene to its initial concentration.

The following two examples show the preparation of and the performance of mordenite catalysts which have Si/Al ratios outside the preferred range of this invention.

EXAMPLE 9

The method of dealumination used in this example generally follows the procedure disclosed in Example 1 of EPA 0,317,907. That EPA also shows a process for the production of 2,6 DIPN.

The first sample (a Toyo Soda Na-Mordenite) was exchanged with 1N—HCl for a period of 30 minutes, rinsed, and calcined for two hours in an oven at 700° C. The treated sample is Example 9(a). The procedure produced a zeolite having an Si/Al ratio of 14, below the desired range.

The second sample began as Example 9(a). It was dealuminated by reflexing the material under 6N—HNO₃ for two hours. The material was washed, dried, and calcined in an oven at 700° C. for two hours. This procedure gave a dealuminated material (Example 9(b)) having a Si/Al ratio of 63, a value above the desired range.

The third material began as a Toyo Soda H-Mordenite. It was calcined in air at 700° C. for two hours, refluxed in 6N—HNO₃ for two hours, washed, rinsed, and again calcined in air at 700° C. for two hours. This procedure resulted in a material (Example 9(c)) haVing a Si/Al ratio of 120, a value above the desired range of this invention but within the most preferred range of EPA '907.

EXAMPLE 10

Each of the samples of Example 9 were then tested for activity using the procedure of Example 8. The results from those runs using each of the three catalysts is shown below:

TABLE 15

Results of isopropylation of naphthalene using the Example 9(a) mordenite catalyst (Si/Al = 14)

| Reaction Time (Hrs) | Conversion | % Mono | % di | % other | 2,6/2,7 ratio | 2,6/DiPN % |
|---|---|---|---|---|---|---|
| 0 | — | — | — | — | — | — |
| 0.5 | 12.2 | 92.2 | 7.8 | 0.0 | 2.36 | 70.2 |
| 1.3 | 19.6 | 88.5 | 11.6 | 0.0 | 1.47 | 56.7 |
| 2.0 | 20.6 | 89.9 | 9.9 | 0.2 | 2.23 | 61.8 |

This run was terminated after two hours because of a lack of activity.

TABLE 16

Results of isopropylation of naphthalene using the Example 9(b) mordenite catalyst (Si/Al = 63)

| Reaction Time (Hrs) | Conversion | % Mono | % di | % other | 2,6/2,7 ratio | 2,6/DiPN % |
|---|---|---|---|---|---|---|
| 0 | — | — | — | — | — | — |
| 0.5 | 34.3 | 76.0 | 23.4 | 0.0 | 3.02 | 71.5 |
| 1.5 | 56.7 | 65.5 | 33.2 | 0.6 | 2.93 | 69.4 |
| 2.5 | 62.0 | 62.5 | 35.9 | 0.8 | 2.88 | 68.3 |
| 3.5 | 69.4 | 55.5 | 42.5 | 1.3 | 2.70 | 66.6 |
| 5.0 | 73.4 | 50.9 | 47.0 | 1.3 | 2.61 | 65.3 |

TABLE 17

Results of isopropylation of naphthalene using the Example 9(c) mordenite catalyst (Si/Al = 120)

| Reaction Time (Hrs) | Conversion | % Mono | % di | % other | 2,6/2,7 ratio | 2,6/DiPN % |
|---|---|---|---|---|---|---|
| 0 | — | — | — | — | — | — |
| 0.5 | 52.5 | 64.0 | 35.6 | 0.3 | 3.28 | 74.0 |
| 1.5 | 71.8 | 52.2 | 47.1 | 0.7 | 3.10 | 71.4 |
| 2.5 | 76.0 | 47.4 | 51.5 | 1.0 | 3.04 | 70.7 |
| 4.0 | 80.8 | 43.4 | 55.2 | 1.1 | 2.98 | 69.6 |
| 5.5 | 84.8 | 39.5 | 59.0 | 1.5 | 2.92 | 68.8 |
| 7.5 | 86.9 | 37.7 | 60.5 | 1.6 | 2.90 | 6S.5 |
| 10.3 | 83.7 | 39.7 | 59.9 | .5 | 2.64 | 67.4 |

As was done with the results above, the reaction progress for each of catalysts Example 9(a), 9(b) and 9(c) was converted to a natural logarithmic plot. Those results are shown in FIG. 3.

Figure 3:
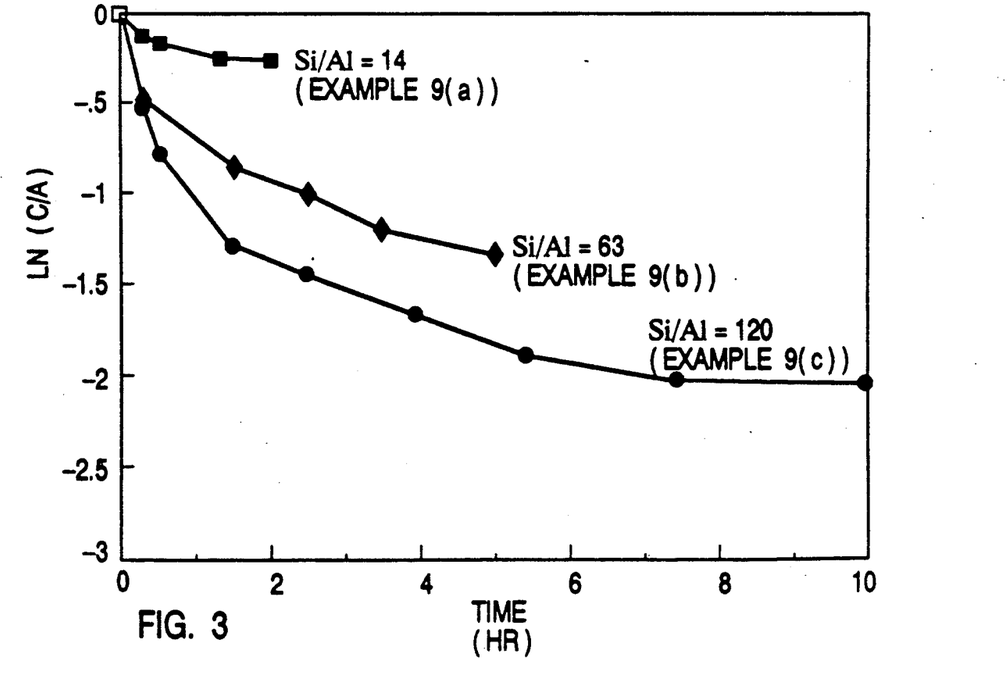

A comparison of the reaction rate plots of materials having the desired Si/Al ranges in FIG. 2 with those for materials outside the desired Si/Al ratio range in FIG. 3 clearly shows a substantially quicker comparative deactivation rate for the non-preferred material.

As additional proof of the preferred nature of the materials within the desired Si/Al ratio of this invention, a second run on several of the catalysts used in Examples 7 and 9 was performed to evaluate the continuing (and comparative) activity of the catalysts.

EXAMPLE 11

The catalyst in Example 7(a) was isolated from the reactor effluent by filtration, introduced into the autoclave reactor, and tested using the same procedure as found in Examples 8 and 10.

TABLE 18

Results of second isopropylation of naphthalene using the Example 7(a) mordenite catalyst (Si/Al = 19)

| Reaction Time (Hrs) | Conversion | % Mono | % di | % other | 2,6/2,7 ratio | 2,6/DiPN % |
|---|---|---|---|---|---|---|
| 0 | — | — | — | — | — | — |
| 0.5 | 23.9 | 80.3 | 19.4 | 0.0 | 2.01 | 62.3 |
| 1.0 | 41.0 | 74.0 | 25.4 | 0.1 | 2.67 | 66.8 |
| 2.0 | 68.6 | 57.6 | 40.6 | 1.3 | 2.75 | 66.3 |
| 2.8 | 76.8˙ | 51.4 | 46.4 | 1.7 | 2.67 | 64.7 |
| 4.2 | 86.5 | 41.9 | 54.7 | 2.7 | 2.64 | 63.4 |
| 5.5 | 89.7 | 38.5 | 57.7 | 3.1 | 2.62 | 62.3 |
| 7.2 | 90.0 | 35.0 | 60.5 | 3.4 | 2.46 | 60.2 |

Figure 4:
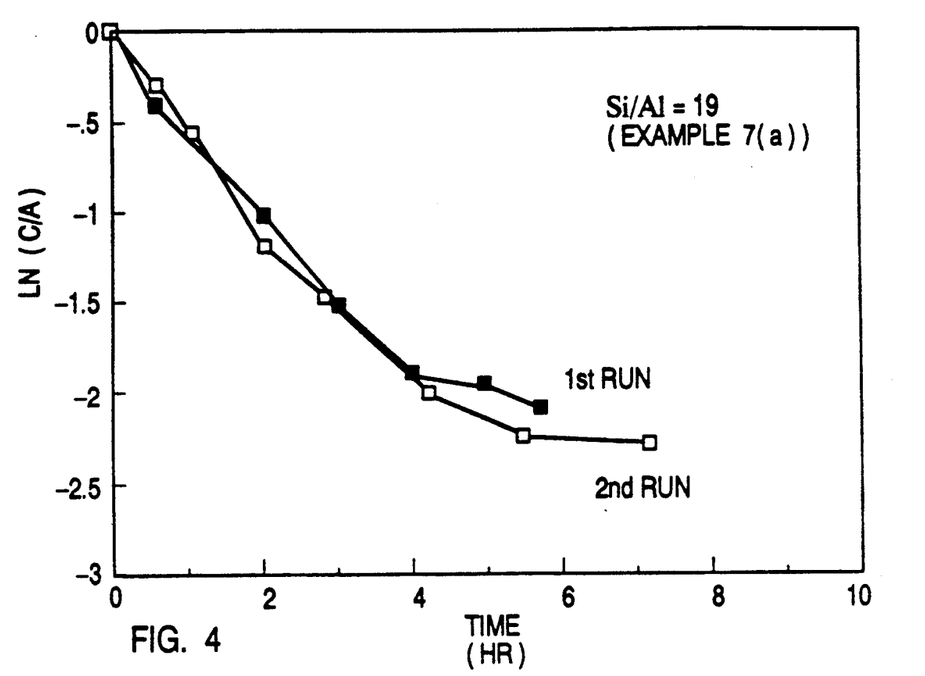

The conversion in this run may be found plotted in natural log form in FIG. 4. The conversion information from a first run using another portion of the Example 7(a) catalyst is placed in this FIG. 4 for ease of comparison. It is clear that the conversion for the second run remained at a level essentially equal to that of the first run.

The two catalysts having high Si/Al ratios and which were within the desired Si/Al ratio range of EPA '907 (Examples 9(b) and 9(c)) were again subjected to a naphthalene isopropylation reaction to measure their ability to maintain naphthalene conversion.

EXAMPLE 12

The catalysts of Examples 9(b) and 9(c) were again subjected to a naphthalene isopropylation using the procedure found in Example 11 as well as in Examples 8 and 10.

TABLE 19

Results of second isopropylation of naphthalene using the Example 9(b) mordenite catalyst (Si/Al = 63)

| Reaction Time (Hrs) | Conversion | % Mono | % di | % other | 2,6/2,7 ratio | 2,6/DiPN % |
|---|---|---|---|---|---|---|
| 0 | — | — | — | — | — | — |
| 0.5 | 8.3 | 79.6 | 20.4 | 0.0 | 1.62 | 61.8 |
| 2 | 21.7 | 81.1 | 18.9 | 0.0 | 2.57 | 69.4 |
| 4 | 33.5 | 77.1 | 22.9 | 0.0 | 2.90 | 70.1 |
| 7 | 33.7 | 74.7 | 25.2 | 0.2 | 2.55 | 67.9 |

TABLE 20

Results and second isopropylation of naphthalene using the Example 9(c) mordenite catalyst (Si/Al = 120)

| Reaction Time (Hrs) | Conversion | % Mono | % di | % other | 2,6/2,7 Ratio | 2,6/DiPN % |
|---|---|---|---|---|---|---|
| 0 | — | — | — | — | — | — |
| 0.5 | 5.2 | 67.0 | 33.0 | 0.0 | 1.37 | 57.9 |

TABLE 20-continued

Results and second isopropylation of naphthalene using the Example 9(c) mordenite catalyst (Si/Al = 120)

| Reaction Time (Hrs) | Conversion | % Mono | % di | % other | 2,6/2,7 Ratio | 2,6/DiPN % |
|---|---|---|---|---|---|---|
| 2 | 9.7 | 81.7 | 18.3 | 0.0 | 1.83 | 64.6 |
| 4.1 | 25.1 | 75.8 | 24.2 | 0.0 | 1.87 | 63.4 |

Figure 5:
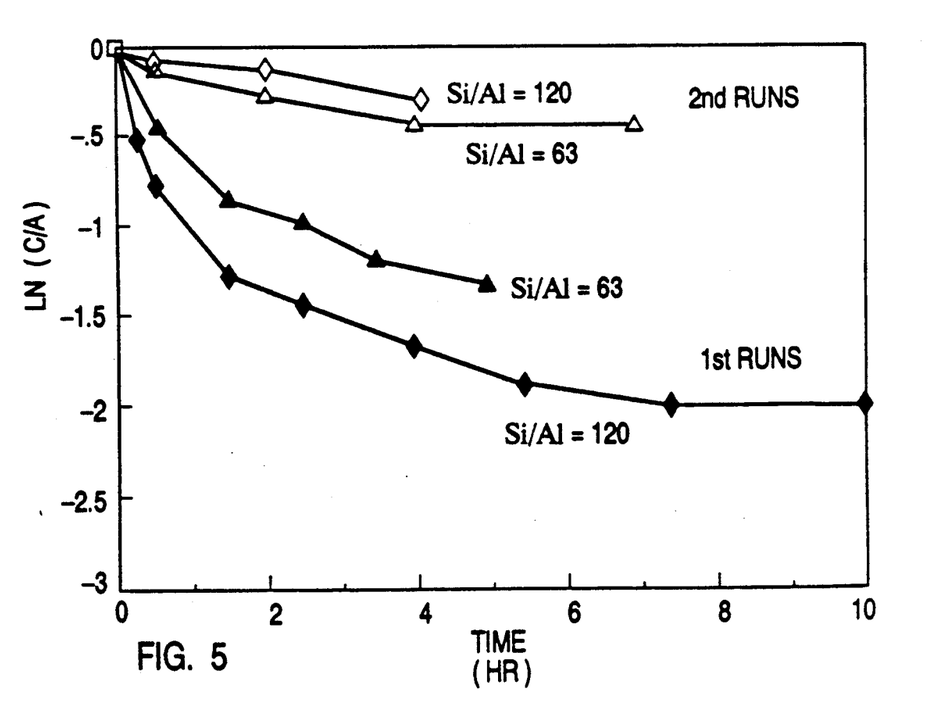

The conversions of naphthalene for these catalysts were converted to natural logarithm plots and portrayed (along with the first run conversions) in FIG. 5.

It is clear that each of the two higher Si/Al Mordenite catalysts (i.e., outside the preferred range of this invention) suffered substantial deactivation during the second run.

Finally, as we noted above, certain of the dealuminated zeolite materials as characterized both by Si/Al ratio and by the NMR ratios discussed above are superior naphthalene diisopropylation catalysts when compared to those taught in EPA '907.

To illustrate this point, catalysts of Examples 9(b) and 9(c) (Si/Al ratios of 63 and 120 respectively) were analyzed using the $^{27}$Si MAN NMR techniques noted above. Additionally, three catalysts (including Example 7(c)) within the most preferred Si/Al ratios of the present invention were similarly analyzed. The following examples illustrate the relationship amongst the NMR ratio, Si/Al ratio, and catalyst effectiveness.

EXAMPLE 13

A sample of Na-mordenite was exchanged twice with an appropriate amount of 5N NH$_4$Cl. After draining and rinsing, the material was steamed for 30 minutes with 400° C. steam and acid leached with 0.5N HCl for four hours. Finally, the washed mordenite was calcined for 12 hours at 500° C. in air. The resulting material had a Si/Al ratio of 17.3 and a NMR ratio of 0.8. The dealuminated mordenite was then used in a diisopropylation reaction using the procedures as found in Examples 8 and 10.

TABLE 21

Results of isopropylation of naphthalene using Example 13 mordenite (Si/Al = 17.3; NMR Ratio = 0.8)

| Reaction Time (Hrs) | Conversion | % Mono | % di | % other | 2,6/2,7 ratio | 2,6/DiPN % |
|---|---|---|---|---|---|---|
| 0 | — | — | — | — | — | — |
| 0.5 | 35.1 | 80.5 | 13.9 | 0.0 | — | 84.5 |
| 1 | 42.6 | 77.3 | 22.4 | 0.3 | 2.66 | 84.5 |
| 2 | 61.9 | 64.8 | 34.4 | 0.7 | 2.31 | 82.9 |
| 3 | 76.9 | 55.9 | 42.8 | 1.2 | 2.36 | 81.0 |
| 4 | 83.6 | 49.7 | 40.5 | 1.6 | 2.26 | 80.2 |
| 5 | 88.6 | 43.1 | 56.6 | — | 2.30 | 82.1 |

Figure 6:
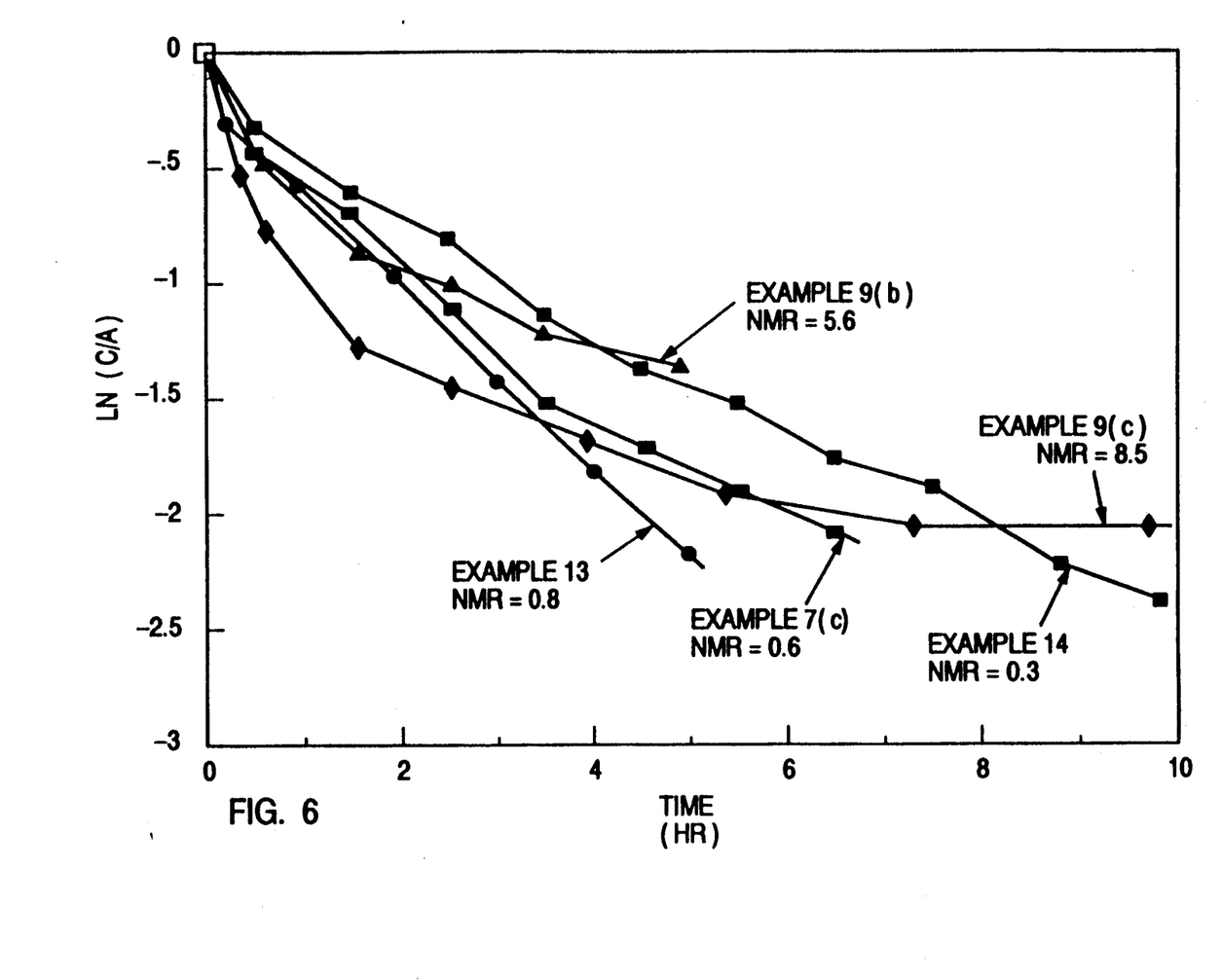

The conversion, as with the other examples, is plotted logarithmically in FIG. 6.

EXAMPLE 14

Similarly, a sample of Na-mordenite was treated using the procedure of Example 13. The resulting material had a Si/Al ratio of 27.9 and an NMR ratio 3. The dealuminated mordenite was then used in a diisopropylation reaction using the procedures of Examples 8 and 10.

TABLE 22

Results of isopropylation of napthalene using Example 13 mordenite (Si/Al = 27.9; NMR Ratio = 0.3)

| Reaction Time (Hrs) | Conversion | % Mono | % di | % other | 2,6/2,7 ratio | 2,6/DiPN % |
|---|---|---|---|---|---|---|
| 0 | — | — | — | — | — | — |
| 0.5 | 27.2 | 82.1 | 17.9 | 0.0 | 3.03 | 70.4 |
| 1.5 | 45.2 | 74.5 | 25.3 | 0.2 | 2.95 | 68.3 |
| 2.5 | 55.1 | 69.1 | 30.7 | 0.2 | 2.80 | 66.2 |
| 3.5 | 67.8 | 62.8 | 36.7 | 0.5 | 2.74 | 64.7 |
| 4.5 | 74.7 | 56.3 | 42.9 | 0.7 | 2.64 | 63.5 |
| 5.5 | 78.0 | 52.3 | 46.8 | 0.8 | 2.50 | 62.0 |
| 6.5 | 82.8 | 50.4 | 48.7 | 0.9 | 2.48 | 61.3 |
| 7.5 | 84.8 | 45.6 | 53.1 | 1.2 | 2.40 | 60.4 |
| 8.8 | 89.2 | 39.0 | 59.1 | 1.7 | 2.31 | 59.3 |
| 9.8 | 90.7 | 36.2 | 61.5 | 2.2 | 2.34 | 59.2 |

The conversion was plotted logarithmically in FIG. 6.

FIG. 6 also contains the conversion lines for preferred catalyst Example 7(c), and catalysts which are outside the preferred Si/Al and NMR ratios, i.e., Examples 9(b) and 9(c). The comparative data for FIG. 6 may be summarized as follows:

TABLE 23

| Catalyst (Example #) | Si/Al | NMR Ratio |
|---|---|---|
| 9(b) | 63 | 5.6 |
| 9(c) | 120 | 8.5 |
| 13 | 17.3 | 0.8 |
| 14 | 27.9 | 0.3 |
| 7(c) | 29.8 | 0.6 |

Reviewing the conversions in FIG. 6 reveals that the two samples (Examples 9(b) and 9(c)) having the NMR ratios higher than 5.0 have declining conversion rates. The materials with NMR ratios below 5.0, in contrast, exhibit continuing conversion. It should be understood that on a plot such as are in FIGS. 2 through 6, a conversion line that goes flat shows that the conversion is stopping. Lines having some vertical slope demonstrate continuing reaction.

The catalyst within the disclosed NMR ratio criteria of this invention show clearly enhanced reaction longevity.

While the invention has been described with reference to preferred embodiments, it will be apparent to those in the art that modifications and changes may be made which still fall within the spirit and scope of the claims appended hereto.

We claim:

1. A process for producing a diisopropylnaphthalene stream enriched in 2,6-diisopropylnaphthalene comprising the steps of:
   (a) contacting a naphthyl compound selected from naphthalene, monoisopropylnaphthalene, and mixtures thereof with propylene in the presence of an acidic crystalline molecular sieve catalyst having twelve membered oxygen rings and pore aperture widths between 5.5Å and 7.0Å which catalyst is dealuminated to obtain a Si/Al ratio between 5–100 and the $^{27}$Al—MAS—NMR ratio is less than 5.0 under conditions sufficient to convert the naphthyl compound and propylene to diisopropylnaphthalene; and
   (b) recovering the diisopropylnaphthalene.

2. The process of claim 1 wherein said diisopropylnaphthalene comprises greater than 39 mole percent of 2,6-diisopropylnaphthalene.

3. The process of claim 1 wherein said diisopropylnaphthalene comprises 2,6-diisopropylnaphthalene and 2,7-diisopropylnaphthalene in a mole ration greater than 1.0.

4. The process of claim 1 further comprising recovering substantially pure 2,6-diisopropylnaphthalene from said diisopropylnaphthalene.

5. The process of claim 1 wherein said catalyst is selected from the group consisting of MeAPSO-46, Offretite, ZSM-46 and synthetic Mordenite.

6. The process of claim 5 wherein said acidic crystalline molecular sieve is synthetic Mordenite.

7. The process of claim 5 wherein said acidic crystalline molecular sieve is ZSM-12.

8. The process of claim 5 wherein said acidic crystalline molecular sieve is Offretite.

9. The process of claim 5 wherein said acidic crystalline molecular sieve is MeAPSO-46.

10. The process of claim 6 wherein the synthetic Mordenite was hydrogen-form Mordenite prior to dealumination.

11. The process of claim 1 wherein said catalyst is calcined at a temperature between 400° C. and 1000° C.

12. The process of claim 11 wherein acidic sites on the external surface of said catalyst are deactivated.

13. The process of claim 5 wherein acidic sites on the external surface of said catalyst are deactivated.

14. The process of claim 13 wherein said catalyst is calcined at a temperature between 400° C. and 1000° C.

15. The process of claim 13 wherein the acidic sites on the external surface of said catalyst are deactivated by contacting the catalyst with a deactivating reagent selected from the group consisting of the halogen, hydrotic and organic derivatives of Groups IIIA, IVA, IVB, and VA.

16. The process of claim 13 wherein the acidic sites on the external surface of said catalyst are deactivated by a process comprising the steps of:
(a) filling the intracrystalline free pore volume of said catalyst with a hydrocarbon to obtain an internally protected catalyst;
(b) treating said internally protected catalyst with an aqueous acid or complexing agent which is insoluble in the hydrocarbon contained within the intracrystalline pores; and, 17. A process for producing a diisopropylnaphthalene stream enriched in 2,6-diisopropylnaphthalene comprising the steps of:
(a) contacting a naphthyl compound selected from naphthalene, monoisopropylnaphthalene, mixtures thereof with propylene in the presence of an acidic crystalline molecular sieve catalyst having twelve membered oxygen rings and pore aperture dimensions which have been reduced to less than about 7.0Å by treatment which catalyst is dealuminated to obtain a Si/Al ratio between 3—100 and the $^{27}Al$—MAS—NMR ratio is less than 5.0 under conditions sufficient to convert the naphthyl compound and propylene to a diisopropylnaphthalene stream; and
(b) recovering the diisopropylnaphthalene.

18. The process of claim 17 wherein said acidic crystalline molecular sieve is selected from the group consisting of Zeolite L, Zeolite Beta, faujasite, and SAPO-5.

19. The process of claim 17 wherein said diisopropylnaphthalene comprises greater than 39 mole percent of 2,6-diisopropylnaphthalene.

20. The process of claim 17 wherein said diisopropylnaphthalene comprises 2,6-diisopropylnaphthalene and 2,7-diisopropylnaphthalene in a mole ratio greater than 1.0.

21. The process of claim 17 wherein said diisopropylnaphthalene comprises a 2,6-diisopropylnaphthalene and 2,7-diisopropylnaphthalene in a mole ratio greater than 1.2.

22. The process of claim 17 further comprising recovering substantially pure 2,6-diisopropylnaphthalene from said diisopropylnaphthalene.

23. The process of claim 17 wherein said treatment comprises deactivating acidic sites on the internal surface of said catalyst with a reagent selected from the group consisting of the halogen, hydrotic and organic derivatives of Groups IIIA, IVA, IVB, and VA.

24. The process of claim 18 wherein said catalyst is calcined at a temperature between 400° C. and 1000° C.

25. The process of claim 24 wherein acidic sites on the external surface of said catalyst are deactivated.

26. The process of claim 18 wherein acidic sites on the external surface of said catalyst are deactivated.

27. The process of claim 26 wherein said catalyst is calcined at a temperature between 400° C. and 1000° C.

28. The process of claim 26 wherein the acidic sites on the external surface of said catalyst are deactivated by contacting said catalyst with a deactivating reagent selected from the group consisting of the halogen, hidrotic and organic derivatives of Groups IIIa, IVA, IVB, and VA.

29. The process of claim 26 wherein the acidic sites on the external surface of said catalyst are deactivated by a process comprising the steps of:
(a) filling the intracrystalline free pore volume of said catalyst with a hydrocarbon to obtain an internally protected catalyst;
(b) treating said internally protected catalyst with an aqueous acid or complexing agent which is insoluble in the hydrocarbon contained within the intracrystalline pores; and
(c) removing said hydrocarbon to recover said catalyst.

* * * * *